(12) United States Patent
Levieux

(10) Patent No.: US 11,564,805 B2
(45) Date of Patent: Jan. 31, 2023

(54) INTERVERTEBRAL CAGE FOR ARTHRODESIS

(71) Applicant: SPINEART SA, Meyrin (CH)

(72) Inventor: Jerome Levieux, Satigny (CH)

(73) Assignee: SPINEART SA, Meyrin (CH)

( * ) Notice: Subject to any disclaimer, the term of this patent is extended or adjusted under 35 U.S.C. 154(b) by 300 days.

(21) Appl. No.: 16/816,687

(22) Filed: Mar. 12, 2020

(65) Prior Publication Data

US 2020/0229945 A1 Jul. 23, 2020

Related U.S. Application Data

(63) Continuation of application No. 15/742,919, filed as application No. PCT/EP2016/066316 on Jul. 8, 2016, now abandoned.

(30) Foreign Application Priority Data

Jul. 16, 2015 (FR) ...................................... 15 56698

(51) Int. Cl.
| | | |
|---|---|---|
| *A61F 2/44* | (2006.01) | |
| *A61F 2/28* | (2006.01) | |
| *A61F 2/30* | (2006.01) | |
| *A61F 2/46* | (2006.01) | |

(52) U.S. Cl.
CPC ............ *A61F 2/4465* (2013.01); *A61F 2/447* (2013.01); *A61F 2002/2835* (2013.01); *A61F 2002/30011* (2013.01); *A61F 2002/3092* (2013.01); *A61F 2002/30593* (2013.01); *A61F 2002/30769* (2013.01); *A61F 2002/30985* (2013.01); *A61F 2002/4629* (2013.01)

(58) Field of Classification Search
CPC ...................................................... A61F 2/4465
USPC ................................................. 623/17.11–17
See application file for complete search history.

(56) References Cited

U.S. PATENT DOCUMENTS

| | | | |
|---|---|---|---|
| 4,206,516 A | 6/1980 | Pilliar | |
| 4,693,721 A * | 9/1987 | Ducheyne | ........... A61F 2/30907 428/605 |
| 5,443,515 A | 8/1995 | Cohen et al. | |
| 2005/0112397 A1 | 5/2005 | Rolfe et al. | |
| 2005/0251257 A1 | 11/2005 | Mitchell et al. | |
| 2009/0130632 A1* | 5/2009 | Tsuru | ...................... A61L 27/56 433/201.1 |

(Continued)

FOREIGN PATENT DOCUMENTS

| | | |
|---|---|---|
| DE | 10 2008 044951 A1 | 8/2009 |
| DE | 0 2013 006282 U1 | 4/2014 |

(Continued)

OTHER PUBLICATIONS

International Search Report, dated Sep. 2, 2016, from corresponding PCT/EP2016/066316 application.

*Primary Examiner* — Eduardo C Robert
*Assistant Examiner* — Tara Rose E Carter
(74) *Attorney, Agent, or Firm* — Nixon & Vanderhye

(57) ABSTRACT

Disclosed is an intervertebral cage for arthrodesis, where at least part of an upper and/or lower contact zone is made of a porous titanium material with a thickness of at least 1 mm and with a porosity of between 50% and 90%, where the diameter of the pores (DP) is between 200 µm and 1 mm, and where the pores have an aperiodic distribution.

7 Claims, 2 Drawing Sheets

(56) References Cited

U.S. PATENT DOCUMENTS

| | | | |
|---|---|---|---|
| 2011/0071635 A1 | 3/2011 | Zhang et al. | |
| 2011/0082564 A1 | 4/2011 | Liu et al. | |
| 2011/0190888 A1* | 8/2011 | Bertele | A61F 2/447 623/17.11 |
| 2012/0312778 A1* | 12/2012 | Ullrich, Jr. | C23C 14/34 451/28 |
| 2013/0325142 A1 | 12/2013 | Hunter et al. | |
| 2014/0107786 A1* | 4/2014 | Geisler | A61F 2/30965 623/17.16 |

FOREIGN PATENT DOCUMENTS

| | | |
|---|---|---|
| FR | 2 889 442 A1 | 2/2007 |
| WO | 03/013396 A1 | 2/2003 |
| WO | 2014/018325 A1 | 1/2014 |

* cited by examiner

INTERVERTEBRAL CAGE FOR ARTHRODESIS

The present invention relates to intervertebral cages for arthrodesis, which are also called "intersomatic cages".

Arthrodesis is a surgical operation in which two bones that are initially movable with respect to each other are fixed. It is performed in order to correct a lesion in a bone region and to eliminate the pain associated with movements of this lesion; it is irreversible. It is also referred to as "fusion".

In humans, degeneration of the intervertebral disc tends to reduce the space within the disc and to narrow the foramina through which the nerve roots issue from the spinal canal. This degeneration represents one of the diseases of the spine. The intervertebral discs, it will be remembered, are located in the vertebral column between two consecutive vertebrae. An intervertebral disc comprises a ring of cartilage provided at its center with a gelatinous nucleus. The intervertebral discs are elastic and thus help absorb the shocks to which a vertebral column is subjected.

The surgical treatment of degeneration of the intervertebral disc may necessitate arthrodesis (fusion) of one or more vertebral segments in the best possible anatomical position. This technique thus makes it possible to definitively block one or more of the intervertebral articulations of the column. In order to restore the normal space and the anatomical sagittal angle of the segment (lordosis), intervertebral cages are implanted between the vertebrae.

The intervertebral cages may be solid or hollow. The hollow intervertebral cages are generally designed as a casing with two orifices, one on the lower face and one on the upper face; the lateral faces may also be openworked.

The surgical treatment generally entails polishing the vertebral plates and employing a bone graft, which is present within the intervertebral cage, when the latter is hollow, and/or around the cage, in order to promote fusion of the vertebrae.

It will be noted that, in surgery of the lumbar spine, these intervertebral cages are often inserted by a posterior approach and that they have a somewhat elongate shape in order to allow them to pass between the roots and the dural sheath.

In the following, the "height" of a cage is understood as the dimension measured in the direction corresponding to the thickness (or height) of an intervertebral disc.

Many studies have been carried out with the aim of promoting fusion of the vertebrae by providing means by which it is possible to improve the compatibility and the relationship of the intervertebral cages with the bone tissue; by way of example, mention may be made of the use of reliefs and/or of porosities on the lower and/or upper face, which may be of such a nature as to make fusion easier.

Since the compatibility and the relationship of the intervertebral cages with the bone tissue are critical parameters for the quality and durability of the surgical treatment, there is an ever present need to improve the relationship between an intervertebral cage and the bone tissue.

To this end, the present invention proposes an intervertebral cage for arthrodesis, composed of:
an upper face and a lower face comprising, respectively, an upper contact zone and a lower contact zone which are intended to contact, respectively, a first vertebra and a second vertebra consecutive to the first vertebra, each of these faces comprising an orifice;
a part connecting the upper face and the lower face, with continuity of material, and configured to form a cavity intended to receive a bone graft, where said cavity opens out at the orifices of each of the upper and lower faces;
where at least part of the upper and/or lower contact zone is made of a porous titanium material with a thickness of at least 1 mm and with a porosity of between 50% and 90%, where the diameter of the pores is between 200 µm and 1 mm, and where the pores have an aperiodic distribution.

"Aperiodic distribution of the pores" is understood as a distribution of the pores according to an aperiodic structure, that is to say according to a structure which is not constructed on the basis of a spatially repeated pattern; such a distribution can also be described as "random" or "stochastic".

By virtue of the present invention, the inventors have been able to show that it is possible to improve the compatibility and the relationship of the intervertebral cages with the bone tissue. Stable and long-lasting fusion is thus obtained. There is good colonization of such an intervertebral cage by the bone tissue, in particular with effective penetration of the bone tissue into the part of the upper and/or lower contact zone made of a porous titanium material. The relationship between an intervertebral cage and the bone tissue is thus advantageously improved.

The present invention is also directed to an intervertebral cage for arthrodesis comprising the features set out in the following embodiments, which may be combined in all technically conceivable configurations:
the porous titanium material is composed of at least 95% by weight of metallic titanium, for example at least 99% by weight of metallic titanium;
the porosity of the porous titanium material is between 60% and 80%;
the diameter of the pores of the porous titanium material is between 500 µm and 900 µm, for example between 700 µm and 800 µm;
the part of the upper and/or lower contact zone made of a porous titanium material occupies a surface area of greater than or equal to 30% of the surface area of the upper and/or lower contact zone, respectively;
the porous titanium material is composed of a plurality of filaments of dense titanium material which are interlaced and in part join each other, where the pores are formed by the space between these filaments, and where the filaments are of a substantially circular cross section with a diameter of between 50 and 500 µm, for example between 100 and 300 µm;
the part connecting the upper face to the lower face, with continuity of material, comprises an opening suitable for receiving a device for gripping said intervertebral cage;
the intervertebral cage is elongate, and in that the length of the upper face and of the lower face is equal to or greater than twice their width, for example with a length of between 15 mm and 40 mm and a width of between 5 mm and 15 mm;
the orifice of the upper face and the orifice of the lower face are elongate, and the length of each of the orifices is equal to or greater than twice their width, for example with a length of between 10 mm and 25 mm and a width of between 3 mm and 8 mm;
the porous titanium material, with a porosity of between 50% and 90%, where the diameter of the pores is between 200 µm and 1 mm and where the pores have an aperiodic distribution, is produced by additive manufacturing (also called 3D printing);

the intervertebral cage is made of a titanium material of substantially constant chemical composition, and the density of the titanium material differs between at least two parts of the cage; according to another embodiment, the intervertebral cage is composed of one or more biocompatible materials and of the porous titanium material, and the chemical composition of said one or more biocompatible materials differs from that of the porous titanium material.

Other features and advantages of the present invention will become clear from the following description of non-limiting embodiments which are illustrated in the attached figures, where:

Figure 1:
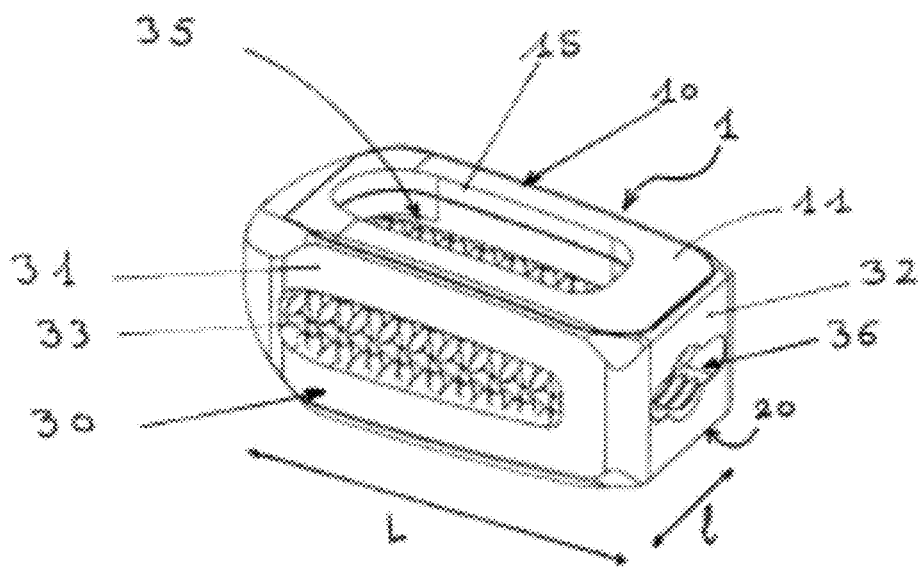
FIGS. 1 and 2 are schematic views of two embodiments of intervertebral cages for arthrodesis.
Figure 2:
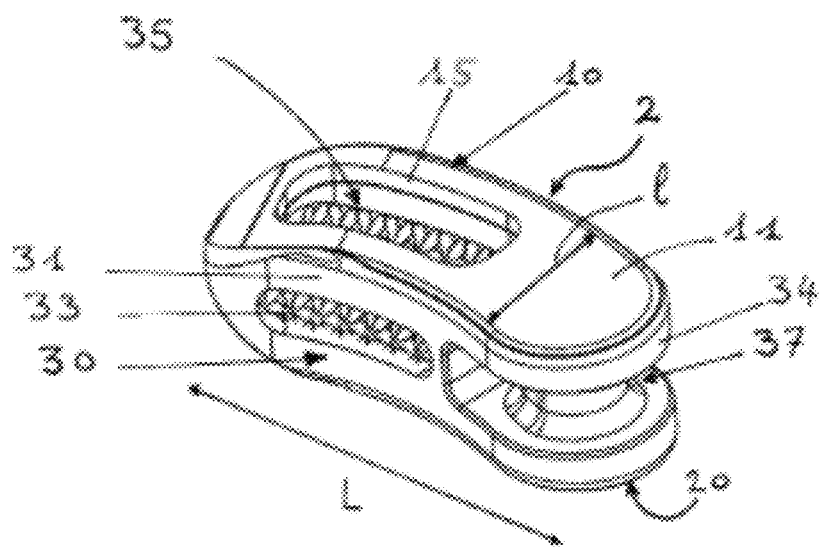

The intervertebral cages for arthrodesis which are shown in FIGS. 1 and 2, and are designated as 1 and 2, respectively, comprise an upper face 10 and a lower face 20; each of these faces comprises a respective contact zone, i.e. an upper contact zone 11 and a lower contact zone (not shown), which are intended to contact, respectively, a first vertebra and a second vertebra consecutive to the first vertebra; each of these faces likewise comprises an orifice 15; in the cages shown, the upper face 10 has mirror symmetry in relation to the lower face 20. The two faces, upper and lower, are opposite each other and are generally slightly inclined with respect to each other, for example by an angle of between 0° and 20°; this angle corresponds to the lordosis between the two consecutive vertebrae. These two faces are connected, with continuity of material, by a part 30. This part 30 comprises in particular a wall which is generally substantially perpendicular to the upper and lower faces. This wall can extend all around the perimeter of the upper and lower faces, as shown in FIG. 1, or around only part of the perimeter of the upper and lower faces, as shown in FIG. 2. This part 30 ensures the mechanical rigidity of the intervertebral cage and is configured to resist the forces applied between two consecutive vertebrae. The part 30 is configured to form a cavity 35 intended to receive a bone graft. Said cavity 35 opens out at the orifices of each of the upper and lower faces. Such intervertebral cages are referred to as "monobloc", and the upper face 10 is not movable with respect to the lower face 20.

The intervertebral cages for arthrodesis in FIGS. 1 and 2 are elongate, and the length L of the upper face (in this case similar to that of the lower face) is equal to or greater than twice their width 1; by way of example, this length is between 15 mm and 40 mm, and this width is between 5 mm and 15 mm.

The part 30 providing a continuous material connection between the upper face and lower face comprises two longitudinal faces 31 arranged along an axis corresponding to the length, and two lateral faces 32 (for FIG. 1) or 34 (for FIG. 2) arranged along an axis corresponding to the width. In the examples shown, the longitudinal faces 31 comprise thinned zones 33, for example formed by a lattice structure. These zones can be partially or completely free of material.

The intervertebral cages for arthrodesis in FIGS. 1 and 2 have an elongate orifice on the upper face (similar to the one on the lower face), and the length of the orifice is equal to or greater than twice its width; for example, this length is between 10 mm and 25 mm and this width is between 3 mm and 8 mm.

The intervertebral cage 1 for arthrodesis in FIG. 1 is substantially parallelepipedal and comprises two parallel longitudinal faces and two parallel lateral faces. These longitudinal and lateral faces are perpendicular to each other and are generally slightly inclined with respect to the normal of the upper face and/or with respect to the normal of the lower face of said cage. One lateral face moreover comprises a cavity 36; this cavity is intended to receive an end of a component forming part of a device for gripping the intervertebral cage; such a gripping device allows the surgeon to manipulate the intervertebral cage and then position it between two vertebrae. In the present example, the cavity arranged on one of the lateral faces is threaded and allows the component forming part of a gripping device to be fixed therein, this component being in the nature of a screw.

The intervertebral cage 2 for arthrodesis in FIG. 2 is crescent-shaped and comprises two curved longitudinal faces parallel to each other. The two lateral faces are substantially of semi-cylindrical shape, each the mirror symmetry of the other, and are tangential to the curved lateral faces. These longitudinal and lateral faces are generally slightly inclined with respect to the normal of the upper face and/or with respect to the normal of the lower face of said cage. One lateral face moreover comprises a zone 37 which is intended to cooperate with an end of a component forming part of a device for gripping the intervertebral cage. In the present example, said zone arranged on one of the lateral faces comprises a cylindrical part situated between the upper face and the lower face of the cage and set back from the perimeters of these faces. This cylindrical part allows the cage to be manipulated with the aid of a gripping device comprising a part in the nature of forceps.

In the present examples according to the invention, the upper and lower contact zones of the upper and lower faces, respectively, of the intervertebral cages shown in FIGS. 1 and 2 are made of a porous titanium material with a thickness of at least 1 mm and with a porosity of between 50% and 90%, where the diameter of the pores (DP) is between 200 μm and 1 mm, and where the pores have an aperiodic distribution.

Figure 3:
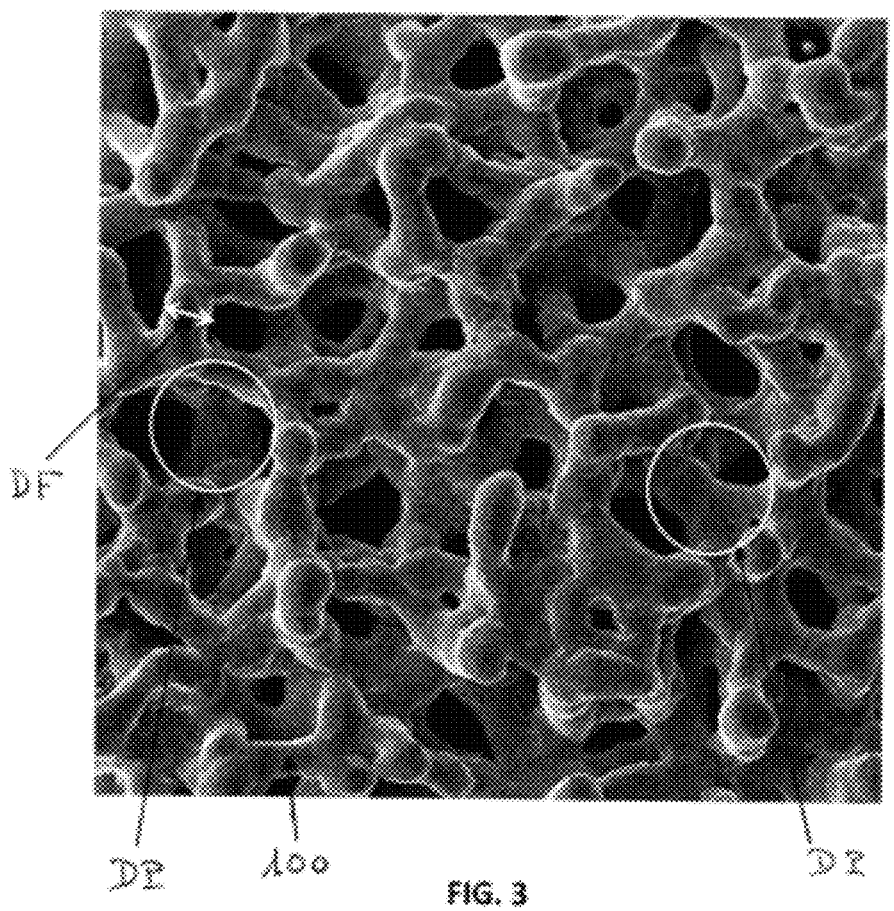
FIG. 3 shows an image of an example of porous titanium material constituting at least part of the upper and/or lower contact zone of an intervertebral cage for arthrodesis according to the present invention.

FIG. 3 shows an image of an example of a porous titanium material of the type in question. This image was taken with an electron scanning microscope, the voltage of the electron beam being regulated at 15 kV. The image is a square, of which the dimension of a side corresponds to a dimension of 3.6 mm. It clearly shows a continuous material composed of a plurality of filaments 100 that join each other at some places and are separated by an empty space at other places. The material is therefore "branched" according to a three-dimensional structure. The filaments, interlaced and in part joined together, are made of dense titanium material. The space between these filaments forms a plurality of pores. In the example shown, the filaments have a substantially circular cross section with a diameter DF substantially equal to 200 μm, and the pores have a diameter DP of substantially between 500 μm and 700 μm. The pores have an aperiodic distribution.

According to one embodiment, the porous titanium material is composed of non-alloyed titanium (containing at least 99% by weight of titanium); according to another embodiment, the porous titanium material is composed of alloyed titanium, for example an alloy comprising aluminum and vanadium, known by the nomenclature Ti6Al4V or TA6V. Such materials are biocompatible.

According to one embodiment, the whole of the intervertebral cage is composed of a single titanium material and only the density of this material varies between parts of the intervertebral cage; according to another embodiment, the intervertebral cage is made of one or more biocompatible materials and of the porous titanium material, and the chemical composition of said one or more biocompatible materials differs from that of the porous titanium material. By way of example, the biocompatible material, different from the porous titanium material, is a polymer, for example known by the name PEEK. In such an example, it is possible to form most of the intervertebral cage from said biocompatible material and to add, to an upper face and/or a lower face of the intervertebral cage, at least one part of the contact zone made of a porous titanium material. Such addition can be done by any technique known to a person skilled in the art and making it possible to "attach" a porous titanium material to another material.

According to one embodiment, the porous titanium material is produced by additive manufacturing (also called 3D printing). "Additive manufacturing" is understood as a manufacturing process involving addition of material, in most cases aided by computer. It is defined by the ASTM as being the process of forming an object by addition of material, layer upon layer, as opposed to subtractive processes involving removal of material, such as machining. Such technology is commonly known as 3D printing. Examples that may be mentioned include laser sintering, in particular selective laser sintering (SLS), direct metal laser sintering (DMLS) or e-beam (EBM). "Printers" use a laser which hardens a metal powder at certain locations in order to give form to the final object. Mention may also be made, by way of example, of processes such as electron beam sintering, known in particular as EBM (electron beam melting).

The invention claimed is:

1. An intervertebral cage for arthrodesis, comprising:
    an upper face and a lower face comprising, respectively, an upper contact zone and a lower contact zone which are intended to contact, respectively, a first vertebra and a second vertebra consecutive to the first vertebra, each of said upper face and said lower face comprising an orifice;
    a part connecting the upper face and the lower face, with continuity of material, wherein said part, said upper face, and said lower face define a cavity therebetween, the cavity being intended to receive a bone graft, where said cavity opens out at the orifices of each of the upper and lower faces;
    wherein at least a part of at least one of the upper and lower contact zone is made of a porous titanium material with a thickness of at least 1 mm and with a porosity of between 60% and 80%, wherein a diameter of pores of the porous titanium material is between 500 µm and 900 µm, and wherein the pores have an aperiodic distribution; and wherein the porous titanium material:
    is a continuous material produced by additive manufacturing (also called 3-dimensional printing) and composed of a plurality of filaments of dense titanium material that join each other at some places and are separated by an empty space at other places; said continuous material being therefore branched according to a three-dimensional structure;
    is of substantially constant chemical composition, and;
    has a density which differs between at least two parts of the cage;
    comprises at least 99% by weight metallic titanium;
    wherein the pores are defined by the space between the filaments, and wherein the filaments are of a substantially circular cross section with a diameter of between 50 µm and 500 µm.

2. The intervertebral cage as claimed in claim 1, wherein the part of the upper and/or lower contact zone made of a porous titanium material occupies a surface area of greater than or equal to 30% of the surface area of the upper and/or lower contact zone, respectively.

3. The intervertebral cage as claimed in claim 1, wherein the part connecting with upper face to the lower face, with continuity of material, comprises an opening suitable for receiving a device for gripping said intervertebral cage.

4. The intervertebral cage as claimed in claim 1, wherein the intervertebral cage is elongate, and wherein a length of the upper face and of the lower face is equal to or greater than twice a width of the upper face and of the lower face, respectively.

5. The intervertebral cage as claimed in claim 1, wherein the orifice of the upper face and the orifice of the lower face are elongate, and a length of each of the orifices is equal to or greater than twice a width of each of the orifices, respectively.

6. The intervertebral cage as claimed in claim 1, wherein the intervertebral cage is made of one or more biocompatible materials and of the porous titanium material, and wherein a chemical composition of said one or more biocompatible materials differs from that of the porous titanium material.

7. The intervertebral cage as claimed in claim 1 wherein the intervertebral cage is elongate, the upper face and of the lower face of said intervertebral cage having a length which is between 15 mm and 40 mm and a width which is between 5 mm and 15 mm.

* * * * *